(12) United States Patent
Zhan et al.

(10) Patent No.: US 12,733,822 B2
(45) Date of Patent: Sep. 15, 2026

(54) HEART RATE AND RESPIRATORY RATE MEASUREMENTS FROM IMAGERY

(71) Applicant: Google LLC, Mountain View, CA (US)

(72) Inventors: Jiening Zhan, Sunnyvale, CA (US); Sean Kyungmok Bae, Rockville, MD (US); Silviu Borac, Pacifica, CA (US); Yunus Emre, Mountain View, CA (US); Jonathan Wesor Wang, Cupertino, CA (US); Jiang Wu, San Jose, CA (US); Mehr Kashyap, Palo Alto, CA (US); Ming Jack Po, Mountain View, CA (US); Liwen Chen, Mountain View, CA (US); Melissa Chung, Emerald Hills, CA (US); John Cannon, Mountain View, CA (US); Eric Steven Teasley, San Francisco, CA (US); James Alexander Taylor, Jr., Seattle, WA (US); Michael Vincent McConnell, Los Altos Hills, CA (US); Alejandra Maciel, San Diego, CA (US); Allen KC Chai, Cerritos, CA (US); Shwetak Patel, Seattle, WA (US); Gregory Sean Corrado, San Francisco, CA (US); Si-Hyuck Kang, Seoul (KR); Yun Liu, Mountain View, CA (US); Michael Rubinstein, Natick, MA (US); Michael Spencer Krainin, Arlington, MA (US); Neal Wadhwa, Cambridge, MA (US)

(73) Assignee: GOOGLE LLC, Mountain View, CA (US)

( * ) Notice: Subject to any disclaimer, the term of this patent is extended or adjusted under 35 U.S.C. 154(b) by 594 days.

(21) Appl. No.: 18/011,899

(22) PCT Filed: Mar. 3, 2022

(86) PCT No.: PCT/US2022/018721
§ 371 (c)(1),
(2) Date: Dec. 21, 2022

(87) PCT Pub. No.: WO2022/187497
PCT Pub. Date: Sep. 9, 2022

(65) Prior Publication Data

US 2023/0277069 A1 Sep. 7, 2023

Related U.S. Application Data

(60) Provisional application No. 63/156,272, filed on Mar. 3, 2021.

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0077* (2013.01); *A61B 5/6898* (2013.01);
(Continued)

(58) Field of Classification Search
CPC ............ A61B 5/02416; A61B 5/02438; A61B 5/0077; A61B 5/0261; A61B 5/6826;
(Continued)

(56) References Cited

U.S. PATENT DOCUMENTS 9,924,870 B2 * 3/2018 Visvanathan .......... A61B 5/327
9,955,880 B2 * 5/2018 Visvanathan ...... A61B 5/02416
2019/0350471 A1 11/2019 Marks et al.

FOREIGN PATENT DOCUMENTS

WO WO 2018/220052 12/2018

OTHER PUBLICATIONS

Aboy et al, "An Automatic Beat Detection Algorithm for Pressure Signals", Transactions on Biomedical Engineering, vol. 52, No. 10, Oct. 2005, pp. 1662-1670.

(Continued)

*Primary Examiner* — Deborah L Malamud
(74) *Attorney, Agent, or Firm* — DORITY & MANNING, P.A.

(57) ABSTRACT

Generally, the present disclosure is directed to systems and methods for measuring heart rate and respiratory rate using a camera such as, for example, a smartphone camera or other consumer-grade camera. Specifically, the present disclosure presents and validates two algorithms that make use of smartphone cameras (or the like) for measuring heart rate (Continued)

(HR) and respiratory rate (RR) for consumer wellness use. As an example, HR can be measured by placing the finger of a subject over the rear-facing camera. As another example, RR can be measured via a video of the subject sitting still in front of the front-facing camera.

20 Claims, 14 Drawing Sheets

(51) Int. Cl.
*A61B 5/024* (2006.01)
*A61B 5/08* (2006.01)

(52) U.S. Cl.
CPC ............ *A61B 5/725* (2013.01); *A61B 5/7257* (2013.01); *A61B 5/7278* (2013.01); *A61B 5/7485* (2013.01); *A61B 5/02416* (2013.01); *A61B 5/0816* (2013.01); *A61B 2576/02* (2013.01)

(58) Field of Classification Search
CPC ... A61B 5/14552; A61B 5/0295; A61B 5/743; A61B 2562/0233; A61B 5/0006; A61B 5/4836; A61B 34/25; A61B 90/361; A61B 2505/07; A61B 5/0059; A61B 5/0082; A61B 5/0205; A61B 5/08; A61B 5/6898; G16H 50/20; G16H 50/70
See application file for complete search history.

(56) References Cited

OTHER PUBLICATIONS

Bashar et al, "Developing a Novel Noise Artifact Detection Algorithm for Smartphone PPG Signals: Preliminary Results", International Conference on Biomedical and Health Informatics, Mar. 4-7, 2018, Las Vegas, Nevada, United States, pp. 79-82.
Chari et al, "Diverse R-PPG: Camera-Based Heart Rate Estimation for Diverse Subject Skin-Tones and Scenes", Cornell University Library, Oct. 24, 2020, 38 pages.
International Search Report for Application No. PCT/ US2022/018721, mailed on Aug. 11, 2022, 5 pages.
Fouladi et al., "Accurate Heart Rate Estimation from Camera Recording via MUSIC Algorithm.", 2015 Thirty-seventh Annual International Conference of the Institute of Electrical and Electronics Engineers, Engineering in Medicine and Biology Society (EMBC), Milan, Italy, Aug. 25-29, 2015, pp. 7454-7457.
International Preliminary Report on Patentability for PCT/US2022/018721, mailed on Sep. 14, 2023, 16 pages.

* cited by examiner

SETUP

USER FACES A SMARTPHONE

HEART RATE AND RESPIRATORY RATE MEASUREMENTS FROM IMAGERY

CROSS-REFERENCE TO RELATED APPLICATIONS

This application is based upon and claims the right of priority under 35 U.S.C. § 371 to International Application No. PCT/US2022/018721 filed on Mar. 3, 2022, which is based on and claims priority to and the benefit of U.S. Provisional Patent Application No. 63/156,272, filed Mar. 3, 2021. Applicant claims priority to and the benefit of each of such applications and incorporates all such applications herein by reference in its entirety.

FIELD

The present disclosure relates generally to heart rate and respiratory rate measurements. More particularly, the present disclosure relates to measuring heart rate and respiratory rate from imagery captured by a camera such as a smartphone camera or other consumer-grade camera.

BACKGROUND

Measurement of heart rate (HR) and respiratory rate (RR), two of the four cardinal vital signs—HR, RR, body temperature, and blood pressure—is often a starting point of physical assessment for both health and wellness. However, taking these standard measurements via a physical examination becomes challenging in telehealth, remote care, remote triage, remote physical assessment, remote monitoring, and consumer wellness settings, which are becoming increasing common. Although specialized measurement devices are commercially available for consumers and have the potential to motivate healthy behaviors, their cost and relatively low adoption limit general usage.

SUMMARY

Aspects and advantages of embodiments of the present disclosure will be set forth in part in the following description, or can be learned from the description, or can be learned through practice of the embodiments.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

One general example aspect includes a computer-implemented method to measure heart rate of a subject. The computer-implemented method includes obtaining, by a computing system that includes one or more computing devices, a plurality of image frames captured by a camera while a digit of the subject is placed in a field of view of the camera. The method also includes measuring, by the computing system, a photoplethysmography (PPG) waveform from the plurality of image frames. The method also includes extracting, by the computing system, a dominant frequency from the PPG waveform. The method also includes determining, by the computing system, the heart rate of the subject based on the dominant frequency extracted from the PPG waveform. Other embodiments of this aspect include corresponding computer systems, apparatus, and computer programs recorded on one or more computer storage devices, each configured to perform the actions of the methods.

Implementations may include one or more of the following features. In some implementations, measuring, by the computing system, the PPG waveform from the plurality of image frames may include: selecting, by the computing system, regions of interest from the plurality of image frames; averaging, by the computing system, pixels in each of the regions of interest on a per-channel basis (e.g. separately for each of a plurality of color channels included in the image frame; e.g. up to three channels in the case of RGB images) to form a plurality of per-channel waveforms; and computing, by the computing system, the PPG waveform as a weighted average of the plurality of per-channel waveforms. Measuring the PPG waveform may include: applying, by the computing system, one or more bandpass filters to the PPG waveform. Measuring the PPG waveform may include: smoothing, by the computing system, the PPG waveform using a maximum allowed change in amplitude which is a function of a moving average of PPG waveform values. Extracting, by the computing system, the dominant frequency from the PPG waveform may include: generating, by the computing system, a fast Fourier transform representation of the PPG waveform; and extracting, by the computing system, the dominant frequency from the fast Fourier transform representation. Extracting, by the computing system, the dominant frequency from the fast Fourier transform representation may include: summing, by the computing system, powers of first, second, and third harmonics. Extracting, by the computing system, the dominant frequency from the PPG waveform may include: determining, by the computing system, a signal to noise ratio for each region of interest by computing a ratio between a power of a dominant frequency and powers of non-dominant frequencies on a logarithmic scale; identifying, by the computing system, the region of interest with the largest signal to noise ratio; and extracting, by the computing system, the dominant frequency of the region of interest with the largest signal to noise ratio. The digit may include a finger. The digit of the subject may be placed in physical contact with an outermost lens or cover of the camera during capture of the plurality of image frames. The computing system may consist of a user device, such as a user device having an integrated camera (e.g. a camera which is within the same cover (housing) as the one or more computing devices).

Another general example aspect includes a computer-implemented method to measure respiratory rate of a subject. The computer-implemented method includes obtaining, by a computing system which may include one or more computing devices, a plurality of image frames captured by a camera while a subject is placed in a field of view of the camera. The method also includes determining, by the computing system, for each pixel of one or more pixels in each frame, a position represented by a phase of spatially localized sinusoids in multiple scales. The method also includes transforming, by the computing system, the phase of the spatially localized sinusoids into optical flow data by linearly approximating the position implied by each phase coefficient and averaging across scales. The method also includes determining, by the computing system, the respiratory rate of the subject based on the optical flow data. Other embodiments of this aspect include corresponding computer systems, apparatus, and computer programs recorded on one or more computer storage devices, each configured to perform the actions of the methods.

Implementations may include one or more of the following features. The computer-implemented method where determining, by the computing system, the respiratory rate of the subject based on the optical flow data may include: selecting, by the computing system, a plurality of regions of interest; averaging, by the computing system, a vertical component of the optical flow data for each of the regions of interest to generate a plurality of respiratory waveforms respectively for the plurality of regions of interest; and determining, by the computing system, the respiratory rate of the subject based on the plurality of respiratory waveforms. Determining, by the computing system, the respiratory rate of the subject based on the plurality of respiratory waveforms may include: generating, by the computing system, a power spectrum from a frequency domain representation of each respiratory waveform; and aggregating, by the computing system, the power spectra for the plurality of respiratory waveforms to obtain a final ensembled power spectrum; and determining, by the computing system, the respiratory rate of the subject based on a maximum power frequency of the final ensembled power spectrum. The computer-implemented method may include defaulting, by the computing system, to a time-domain estimation of the respiratory waveform when a signal to noise ratio associated with the frequency domain representation falls below a threshold. In some implementations, a base of a neck, a shoulder line, and an upper torso of the subject may be depicted by the plurality of image frames. Implementations of the described techniques may include hardware, a method or process, or computer software on a computer-accessible medium.

Another general example aspect includes a computer-implemented method to measure respiratory rate of a subject. The computer-implemented method includes obtaining, by a computing system may include one or more computing devices, a plurality of image frames captured by a camera while a subject is placed in a field of view of the camera. The method also includes determining, by the computing system, optical flow data for the plurality of image frames. The method also includes averaging, by the computing system, a vertical component of the optical flow data to generate a respiratory waveform. The method also includes generating, by the computing system, a frequency domain representation of the respiratory waveform. The method also includes determining, by the computing system, the respiratory rate of the subject based on the frequency domain representation of the respiratory waveform. Other embodiments of this aspect include corresponding computer systems, apparatus, and computer programs recorded on one or more computer storage devices, each configured to perform the actions of the methods.

A computing device may include: a camera; one or more processors; and one or more non-transitory computer-readable media that collectively store instructions that, when executed by the one or more processors, cause the computing device to perform any of the methods described herein. One or more non-transitory computer-readable media may collectively store instructions that, when executed by one or more processors, cause a computing device to perform any of the methods described herein. Implementations of the described techniques may include hardware, a method or process, or computer software on a computer-accessible medium. These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

Detailed discussion of embodiments directed to one of ordinary skill in the art is set forth in the specification, which makes reference to the appended figures, in which.

Figure 1A:
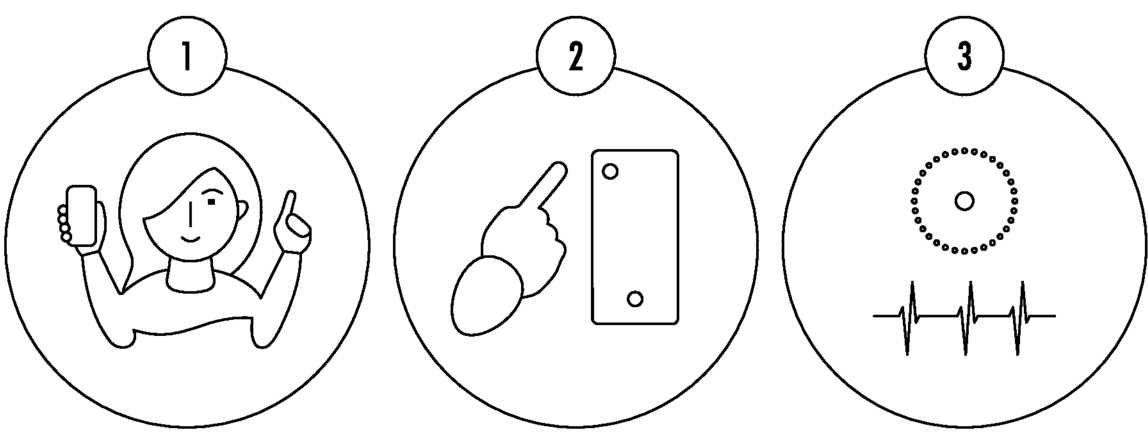
FIG. 1A shows an example "setup" of how measurements are taken—with the finger over the rear-facing camera for HR according to example embodiments of the present disclosure.

Reference numerals that are repeated across plural figures are intended to identify the same features in various implementations.

DETAILED DESCRIPTION

Overview

Generally, the present disclosure is directed to systems and methods for measuring heart rate and/or respiratory rate using a camera such as, for example, a smartphone camera or other consumer-grade camera. Specifically, the present disclosure presents and validates two algorithms that make use of smartphone cameras (or the like) for measuring heart rate (HR) and respiratory rate (RR) for consumer wellness use. As an example, HR can be measured by placing the finger of a subject over the rear-facing camera and/or front-facing camera. As another example, RR can be measured via a video of the subject sitting still in front of the front-facing camera and/or rear-facing camera.

More particularly, a first example approach for HR measurement leverages photoplethysmography (PPG) acquired using cameras, such as consumer-grade and/or embedded cameras such as those commonly found in laptops, tablets, smartphones, and/or user devices (e.g., front-facing and/or rear-facing cameras). PPG signals can be recorded by placing a finger over the camera lens, and the color changes captured in the video can be used to determine the oscillation of blood volume after each heartbeat.

A second example approach measures RR from upper-torso videos obtained via a camera to track the physical motion of breathing. For example, a computing system can determine, for each pixel of one or more pixels in each video frame, a position represented by a phase of spatially localized sinusoids in multiple scales. To express this in another way, a plurality of sinusoidal functions ("sinusoids") may be defined, each function describing an oscillatory average motion of respective corresponding portions of the video frames (e.g. one such sinusoidal function may describe oscillations in a top right corner portion of each of the video frames). The portions of the video frame corresponding to different ones of the sinusoidal functions overlap and have different corresponding sizes (scales). One of the parameters defining each sinusoidal function is a respective phase coefficient. Others of the parameters may be an amplitude of the motion, and parameters describing the portion of the video frames described by the sinusoidal function. Determining, for each of the one or more pixels, a position represented by the phase of the sinusoids can be considered as meaning that the one or more pixels are used to determine some or all parameters of the sinusoidal functions (e.g. the amplitude and the phase coefficient of each sinusoidal function), and in particular the phase coefficients of the plurality of sinusoidal functions. The sinusoids collectively imply, for each of the one or more pixels, a respective position on the subject which is shown by that pixel in any given one of the video frames. The computing system can transform the phase of spatially localized sinusoids into optical flow data by linearly approximating the position implied by each phase coefficient and averaging across scales (e.g. averaging over the sinusoidal functions, to determine the motion collectively implied by them). The computing system can determine the respiratory rate of the subject based on the optical flow data. Optical flow can refer to the pattern of the apparent motion of the subject in the video frames, caused by the motion of the subject relative to the camera. Optical flow can be assessed, for example, on a pixel-by-pixel basis.

The present disclosure reports the performance of these two algorithms in prospective clinical validation studies, demonstrating reliable and consistent accuracy on diverse populations (e.g., in terms of objectively-measured skin tones) for HR and health status (e.g., with and without chronic pulmonary conditions) for RR.

Specifically, in an example HR study of 95 participants (with a protocol that included both measurements at rest and post exercise), the mean absolute percent error (MAPE) ±standard deviation of the measurement was 1.6%±4.3%, which was significantly lower than the pre-specified goal of 5%. No significant differences in the MAPE were present across colorimeter-measured skin-tone subgroups.

In an example RR study of 50 participants, the mean absolute error (MAE) was 0.78±0.61 breaths/min, which was significantly lower than the pre-specified goal of 3 breath/min. The MAE was low in both healthy participants (0.70±0.67 breaths/min), and participants with chronic respiratory conditions (0.80±0.60 breaths/min). These results validate that smartphone camera-based techniques can accurately measure HR and RR across a range of pre-defined subgroups.

The systems and methods described herein provide a number of technical effects and benefits. More particularly, the systems and methods of the present disclosure provide improved techniques for providing a diagnosis (e.g., measuring heart rate and/or respiratory rate) from imagery captured by a camera such as a smartphone camera or other consumer-grade camera. In addition, measured heart rate and/or respiratory rate can improve the accuracy of diagnoses and patient outcomes. As such, the disclosed system can significantly reduce the cost and time needed to provide diagnostic information and can result in improved medical care for patients.

In particular, the present disclosure provides specific algorithmic approaches for measuring heart rate and/or respiratory rate from imagery captured by a camera such as a smartphone camera or other consumer-grade camera. The example experimental results described herein show that example implementations of the proposed systems were able to accurately measure heart rate and/or respiratory rate from imagery captured by a camera such as a smartphone camera or other consumer-grade camera.

The proposed techniques have implications for a very large population of patients because they do not, in principle, require specialized equipment. Specifically, to date, measurement of heart rate and/or respiratory rate has required specialized equipment and/or a trained professional. This limits evaluation of a patient's health to in-person visits. By contrast, the proposed techniques require only imagery of the user's (e.g., the user's finger, torso, etc.). Therefore, improved access to medical care is enabled. Similarly, the computational costs associated with obtaining accurate heart rate and/or respiratory rate measurements can be reduced.

Further to the descriptions above, a user may be provided with controls allowing the user to make an election as to both if and when systems, programs, or features described herein may enable collection of user information (e.g., photographs). In addition, certain data may be treated in one or more ways before it is stored or used, so that personally identifiable information is removed. For example, a user's identity may be treated so that no personally identifiable information can be determined for the user. Thus, the user may have control over what information is collected about the user, how that information is used, and what information is provided to the user.

In some implementations, an entirety of the measurement algorithm(s) is implemented at a single device (e.g., the patient's device, the medical professional's device, a server device, etc.). In other implementations, some portions of the measurement algorithm(s) can be implemented at a first device (e.g., the patient's device or the medical professional's device) while other portions of the algorithm(s) can be implemented at a second device (e.g., a server device). In such fashion, in some implementations, certain data such as patient images and/or patient metadata may never leave the local device (e.g., the patient's device). Instead, in some implementations, only an intermediate data that is less interpretable is transmitted from the local device to the server device. This arrangement can improve patient privacy.

Thus, the present disclosure demonstrates the surprising result that heart rate and respiratory rate can be measured using only imagery captured by a low-cost, general consumer grade camera (e.g., as included in a smartphone, tablet, laptop, etc.). The tool can be used in a home, pharmacy, or primary care setting to improve disease screening and help with diagnosis and management of disease.

With reference now to the Figures, example embodiments of the present disclosure will be discussed in further detail.

Example Studies and Results

Two separate example prospective studies were conducted to validate the performance of smartphone-based HR and RR measurements. The HR algorithm used PPG signals measured from the study participants placing their finger over the rear camera, and the enrollment for the corresponding validation study was stratified to ensure diversity across skin tones. The RR algorithm used video captures of the face and upper torso, and the enrollment for the corresponding validation study was stratified to capture participants with and without chronic respiratory conditions. The following sections detail each of the two studies. While these algorithms used in these example studies demonstrate aspects of the present disclosure, the present disclosure is not limited to the example algorithms used in the studies.

Example HR Measurement Study

Example Setup and Overview of Results

Figure 1B:
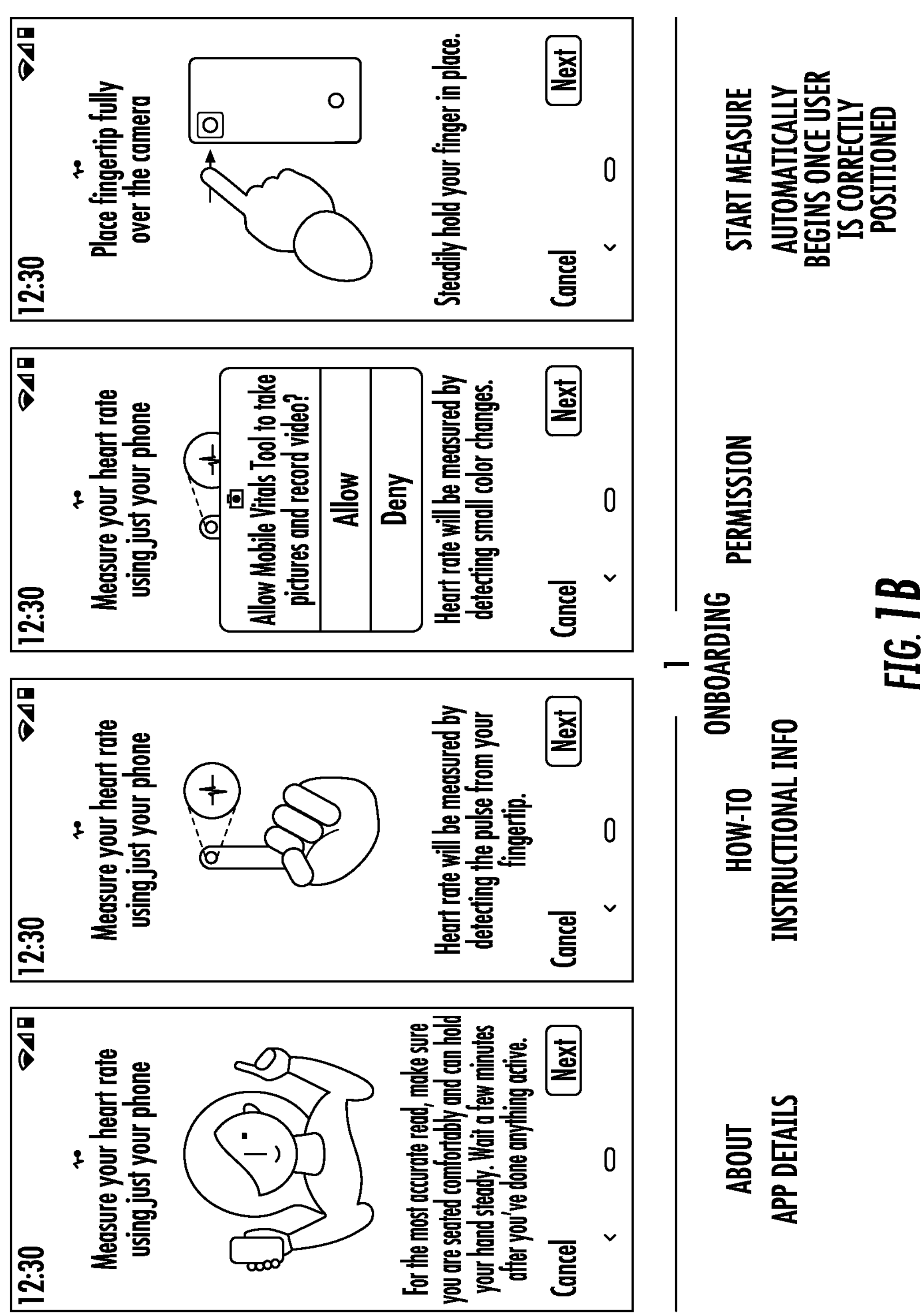
FIGS. 1B-C show example user interfaces for guiding a user to perform the HR evaluation according to example embodiments of the present disclosure.
Figure 1C:
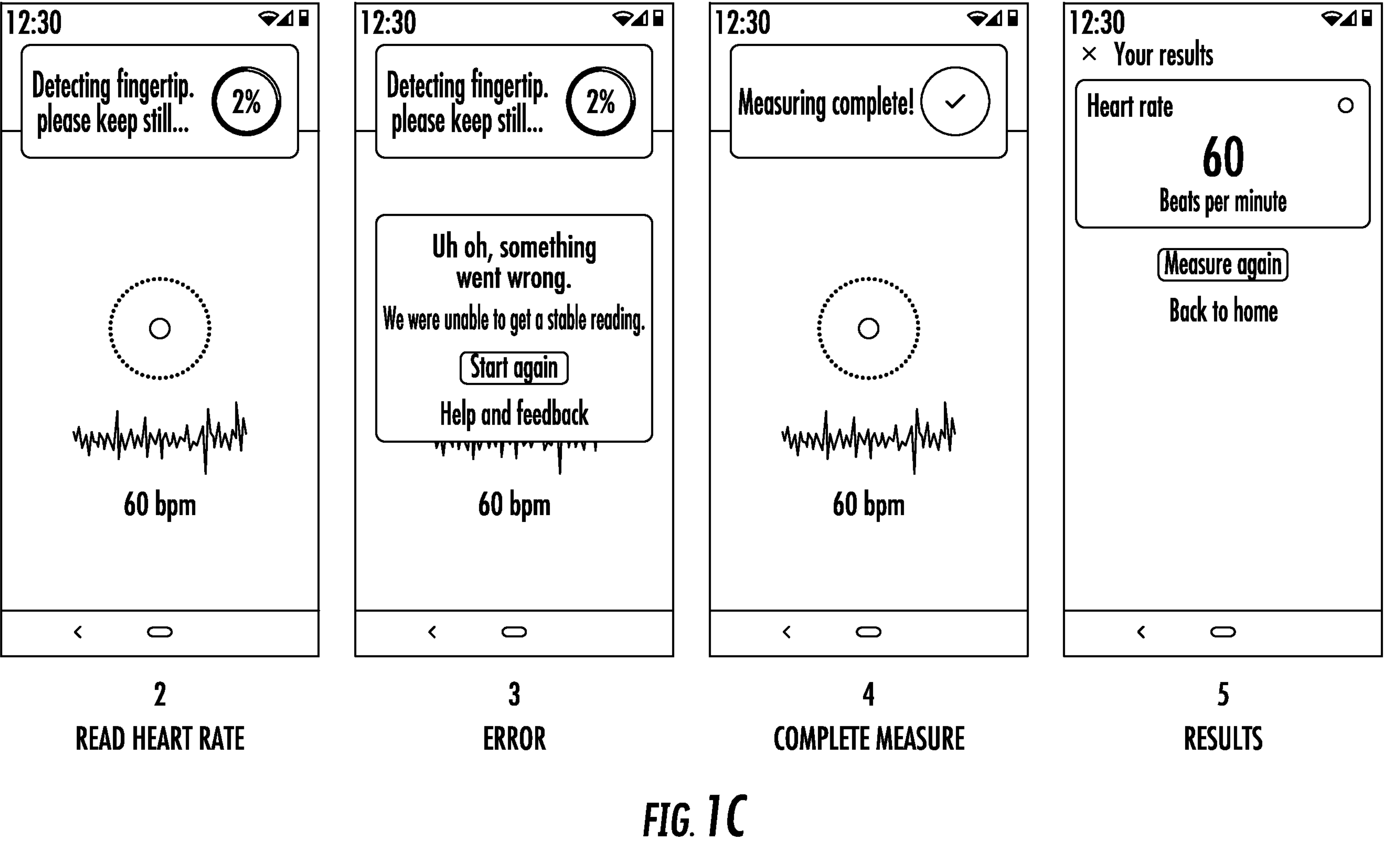
Figure 1D:
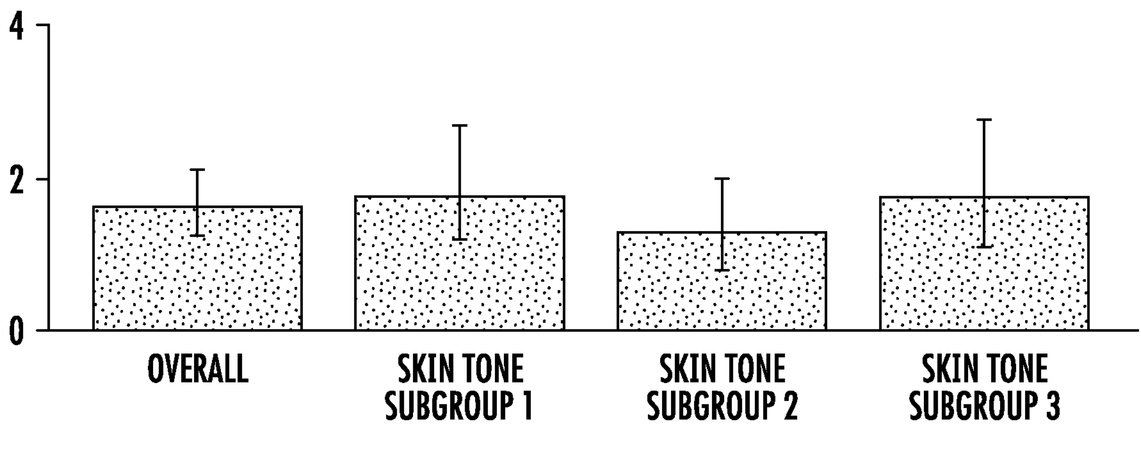
FIG. 1D shows the measurements/results for mean absolute percent error (MAPE) for HR according to example embodiments of the present disclosure.

FIG. 1A shows an example "setup" of how measurements are taken using a user device having an integrated camera, such as a rear-facing camera—with the finger over the rear-facing camera for HR. FIGS. 1B-C show example user interfaces for guiding a user to perform the HR evaluation. Following an onboarding process of FIG. 1B, a plurality of image frames at a series of respective times, e.g. video frames, are captured. The first diagram of FIG. 1C shows the display on a screen of user device at a moment during this process, and the fourth shows a display of the result. FIG. 1D shows the measurements/results for mean absolute percent error (MAPE) for HR.

Example Algorithm Description

An example algorithm provided by the present disclosure estimates HR by optically measuring the PPG waveform from participants' fingertips and then extracting the dominant frequency. First, several rectangular regions of interest (ROI) can be selected (e.g., manually or automatically) from the video frames (e.g., linear RGB at 15 frames per second and at a resolution of 640×480 pixels). The chosen ROIs in some examples can be the full frame, the left half, the right half, the top half, and the bottom half of the frames. Since camera pixels are illuminated non-homogeneously, signal strength can have spatial variations across pixels. Thus, some example implementations of the proposed method simultaneously analyze different ROIs to identify one with the greatest signal-to-noise ratio (SNR).

Pixels in each ROI can be averaged per-channel (e.g. separately for a plurality of color channels, a respective average is formed, over the pixels of the ROI, of the intensity values for each channel) to reduce the effects of sensor and quantization noise. For example, if the images are RGB images, this could be done for each of the RGB channels, to obtain a respective intensity value for each channel and each ROI in each of the image frames. For each given one of the ROIs and each of the channels, the corresponding intensity values over the set of image frames form a respective waveform, e.g. a smoothed (temporal) signal. The pulsatile blood volume changes were present as the AC components in these smoothed signals. The three RGB waveforms can then be weighted to predict a single PPG waveform (e.g., weights 0.67, 0.33, and 0 for RGB respectively were empirically determined via grid search) for each ROI. Note that in the case that one or more of the channels (e.g. blue) is determined to be of low importance, it may be omitted from the per-channel averaging.

The resulting single PPG waveforms for each ROI can be bandpass filtered, e.g. based on respective high and/or low frequency thresholds, to remove low- and/or high-frequency noise unlikely to be valid HR. Example filter cut-off frequencies (thresholds) corresponded to a low of 30 beats/min and high of 360 beats/min. Next, large amplitude changes in PPGs due to motion can be suppressed by limiting maximum allowed changes in amplitudes based on an amplitude change threshold, such as for example 3× of moving average values. Then, frequency domain representations of PPGs can be computed using the Fast Fourier Transform (FFT), from which the dominant frequencies with maximum power can be identified (e.g. a respective dominant frequency for each ROI). That is, for each of a plurality of frequencies (e.g. narrow frequency range), for each ROI a respective power of the frequency may be calculated (the respective amplitude of the FFT), and the frequency with maximum power can be identified. Optionally, the respective power for each at least some of the frequencies ("base frequencies") can be augmented based on the power of one or more harmonics of that frequency. For example, because the PPG signals are periodic with multiple harmonics, optionally the powers of the base frequencies can be computed by a process comprising summing the powers of their first, second, and third harmonics (e.g. and adding the resulting sum to the power of the base frequency). SNRs can be estimated for each ROI by computing the ratio between the power of the dominant frequency and the powers of non-dominant frequencies (e.g. a sum of the respective powers output by the FFT of the frequencies other than the dominant frequency) on a logarithmic scale. ROIs can be filtered to only those with a SNR greater than a threshold (e.g. >0 dB). The dominant frequency of the ROI with the highest SNR can be reported. If no such ROI exists, then the reporting can indicate no HR. In a variant, the reporting can indicate no HR if two or more of the ROI both have the highest SNR and have respective dominant frequencies which differ by more than a threshold amount.

Example Study Design and Participants

An example study performed a prospective observational clinical validation study to assess the accuracy of the study algorithm in estimating HR in individuals. In an attempt to ensure that the algorithm provides benefits for all potential users from diverse groups of people, the study included participants having diverse skin tones. Specifically, study enrollment was stratified into 3 skin-tone subgroups (mapped to Fitzpatrick skin types) to ensure and evaluate broad representation. In an attempt to objectively measure skin tone, readings from participants' cheek skin were collected using a Pantone Capsure color matcher colorimeter (X-Rite, Grand Rapids, MI).

Example Data Collection

Each participant underwent four 30-second data collection episodes with their index finger (of a hand of their choice) held directly over the study phone camera. Three of the 30-second episodes were collected at rest under various ambient brightness/lighting conditions: (1) with camera flash on and under regular ambient light, (2) with flash off and under regular ambient light, and (3) with flash off and under dim light. The fourth episode was collected post-exercise. In the original protocol, participants were instructed to ride a stationary bicycle for 30 seconds as strenuously as possible against light to medium resistance. After enrolling 37 participants, the exercise protocol was modified (with an IRB (Institutional Review Board) amendment) to achieve higher participant HR: participants were encouraged to achieve 75% of their maximal HR, which was calculated by subtracting the participant's age from 220 beats/min. Exercise was completed either when the goal HR was achieved or when the participant asked to stop. The data were collected with flash off and under regular ambient light. Lighting conditions were controlled using two overhead and one front light emitting diode (LED) lights. The brightness level of the study environment was measured by a Lux meter (LT300 Light Meter, Extech, Nashua, NH) prior to each study. Measured brightness values were between 160 and 200 Lux for regular ambient light, and between 95 and 110 Lux for dim light.

The study was conducted using a mobile app deployed to a Pixel 3 smartphone running Android 10 (Google LLC, Mountain View, CA). HR estimation using the app was generally completed by the study participants following the in-app instructions, with the coordinators providing feedback on usage when needed. The reference HR was measured simultaneously during each data collection episode using a Masimo MightySat® (Masimo, Irvine, CA), which is US Food and Drug Administration-cleared for fingertip measurement of pulse rate. The measurements were conducted in accordance with the vendor's manual and taken at the end of each episode.

Example Statistical Analysis

Each participant contributed up to 3 HR measurements at rest (with different lighting conditions), and up to 1 post-exercise. Measurements were paired observations: the algorithm-estimated HR and the reference HR from the pulse oximeter. For each algorithm measurement, up to three tries were allowed, and the number of tries required was recorded. The baseline characteristics (e.g., demographic information, skin characteristic information) of the participants who did not successfully complete algorithm estimation were compared with the rest of the study population using Fisher's exact test. A paired measurement was dropped if either the algorithm estimation or reference measurement failed.

The absolute error of each paired measurement was calculated as the absolute value of the difference between the algorithm-estimated and reference HR values. The mean absolute error (MAE) was the mean value of all absolute errors. Similarly, the absolute error from each paired measurement was divided by the reference value for that measurement and multiplied by 100 to produce the absolute percentage error. The mean absolute percentage error (MAPE) was the mean value for all absolute percent error values. The four (three at rest and one post-exercise; fewer if missing data) values from each participant were treated as statistically independent as the clustering effects (intra-participant correlation) were observed to be minimal.

The MAPE was the primary study performance criterion, as recommended by the current standards for HR monitoring devices. The standard deviation and 95th percentiles were also computed. Sign tests were used to determine whether the absolute percentage errors were significantly <5%, both for the entire group of participants and the 3 skin-tone subgroups. Bland-Altman plots were used to visualize the agreement between the estimated values and the reference measurements and assess for any proportional bias (trends in the error with increasing values). The subgroup analysis across the three skin-tone subgroups was pre-specified.

Example Sample Size Calculation

HR data collection was planned for approximately 100 participants. Enrollment up to a maximum of 150 participants was allowed as it was anticipated that some enrolled participants would be excluded prior to contributing HR data because they failed to meet the required skin tone distribution or because they were not able to exercise. Requirements for participant enrollment termination included ≥60 paired HR measurements in the dark skin tone subgroup and ≥20% of the post-exercise reference HR>100 beats/min. The study hypothesis was that MAPE was less than 5% in all of the 3 skin-tone subgroups. To estimate the sample size required for the study, an IRB-approved feasibility study was first conducted with a different set of 55 participants and similar measurements both at rest and post-exercise. In that study, the MAPE±standard deviation was 0.91%±3.68%. Assuming double the mean and SD (e.g., 1.82% and 7.36%, respectively), a minimum of two paired measurements per participant, a skin-tone subgroup of ~25 participants, and some dropout from incomplete data, the power to detect a MAPE>5% was >0.8.

Example Results

A total of 101 participants were enrolled. After excluding one participant who was found to meet exclusion criteria, there were 100 valid enrollees. Among these, 3 were withdrawn due to skin tone distribution requirements, and 2 were withdrawn during data collection due to difficulty in data collection (such as inability to hold a phone properly or to obtain reference HR data). Thus, 95 participants completed data collection. The participants had a mean age of 41.8 years, 75% were female, and skin-tone subgroups were evenly distributed as planned: 33% were subgroup 1 (very light, light and intermediate), 34% were subgroup 2 (tan and brown), and 34% were subgroup 3 (dark).

From these participants, 379 total recordings were attempted. A valid HR was successfully obtained (see details on SNR in Methods) in 361 cases (95.3%). The success rate increased with retries up to 3 times: 316 measurements (83.4%) were successful on the first try, another 31 measurements (cumulative 91.6%) on the second try, and another 14 measurements (cumulative 95.3%) on the third try. The baseline characteristics of the 14 participants for whom HR values were not successfully reported by the study app for at least one measurement (due to low SNR) did not differ significantly from the remaining participants. In addition, a corresponding valid reference HR was not obtained for 9 recordings from 4 participants. The remaining 352 recordings with paired valid reference HR contributed to the final analysis. The average reference HR was 79.8±14.6 beats/min overall, 75.5±11.2 beats/min at rest, and 92.9±16.6 beats/min post-exercise.

Compared to the reference HR, the MAPE of the overall study population was 1.63%, which was significantly lower than the pre-specified study target of 5% ($p<0.001$). The MAPE of 1.45% at rest and 2.39% post-exercise were also lower than the 5% target ($p<0.001$ for both). The MAPE showed a left-skewed distribution with a long tail (median, 1.14%; range, 0.0-50.6%). The MAPE by skin-tone subgroup was 1.77% for subgroup 1, 1.32% for subgroup 2, and 1.77% for subgroup 3, all of which met the study target of <5% ($p<0.001$ for all subgroups). No significant variation in MAPE was found across the three different lighting conditions.

Example RR Measurement

Example Setup and Overview of Results

Figure 1E:
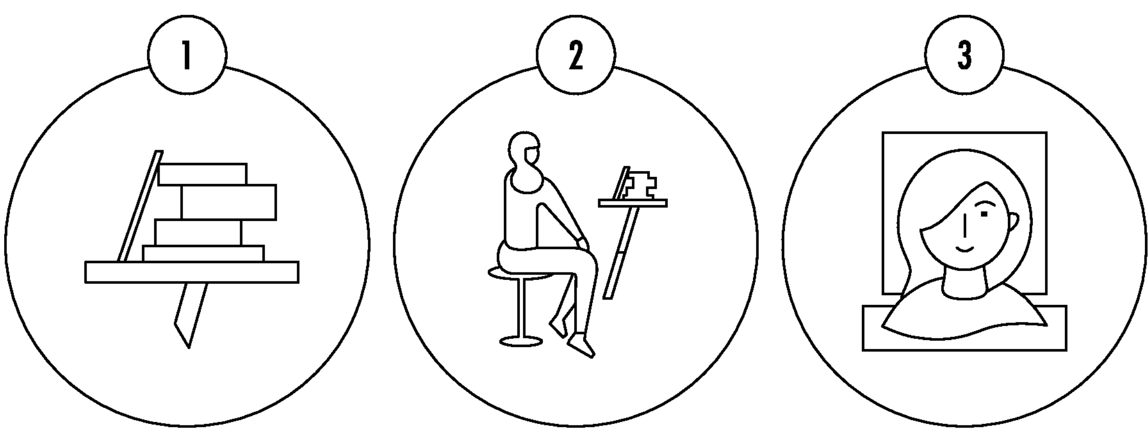
FIG. 1E shows an example "setup" of how measurements are taken using a video of the participant via the front-facing camera according to example embodiments of the present disclosure.
Figure 1F:
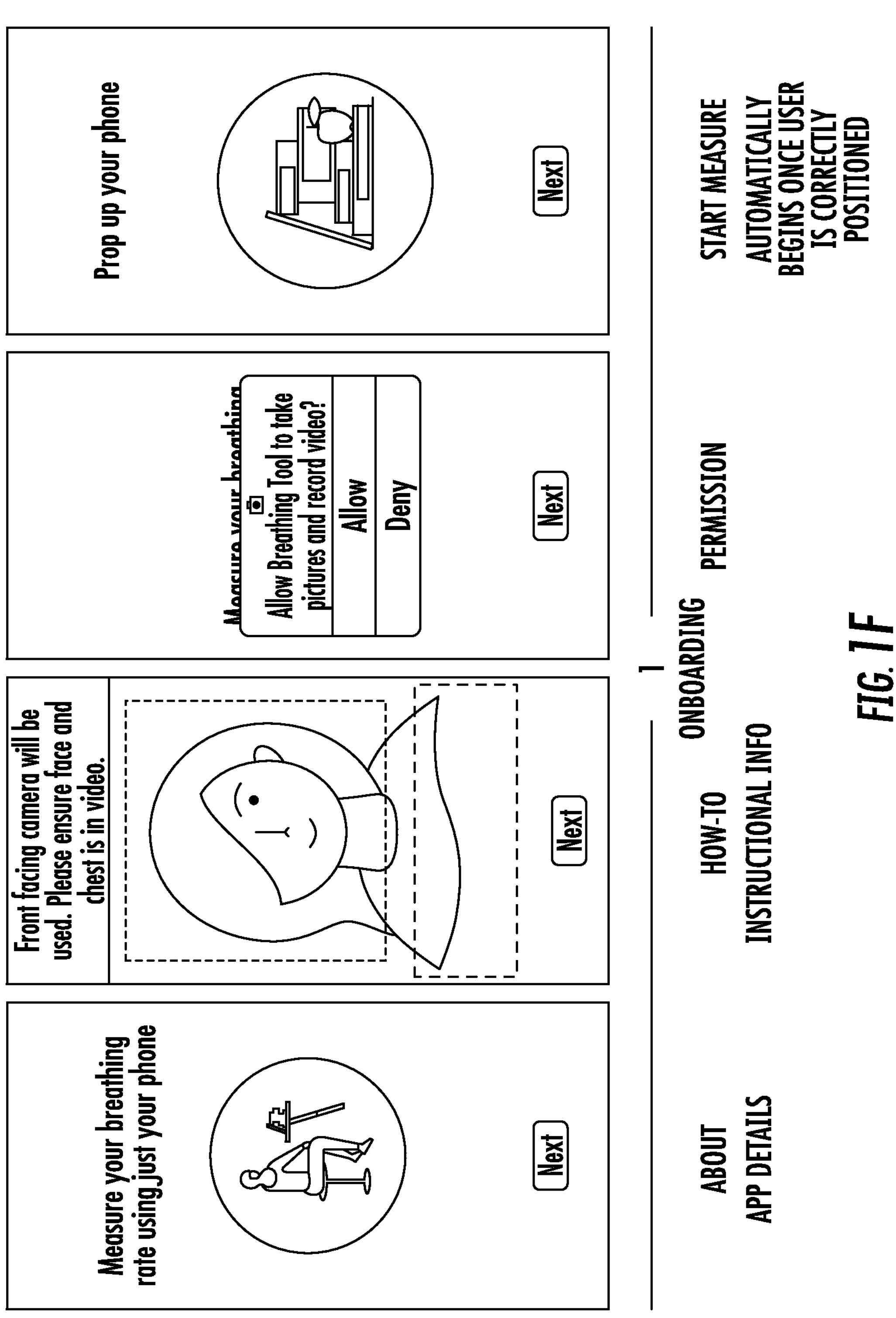
FIGS. 1F-G show example user interfaces for guiding a user to perform the RR evaluation according to example embodiments of the present disclosure.
Figure 1G:
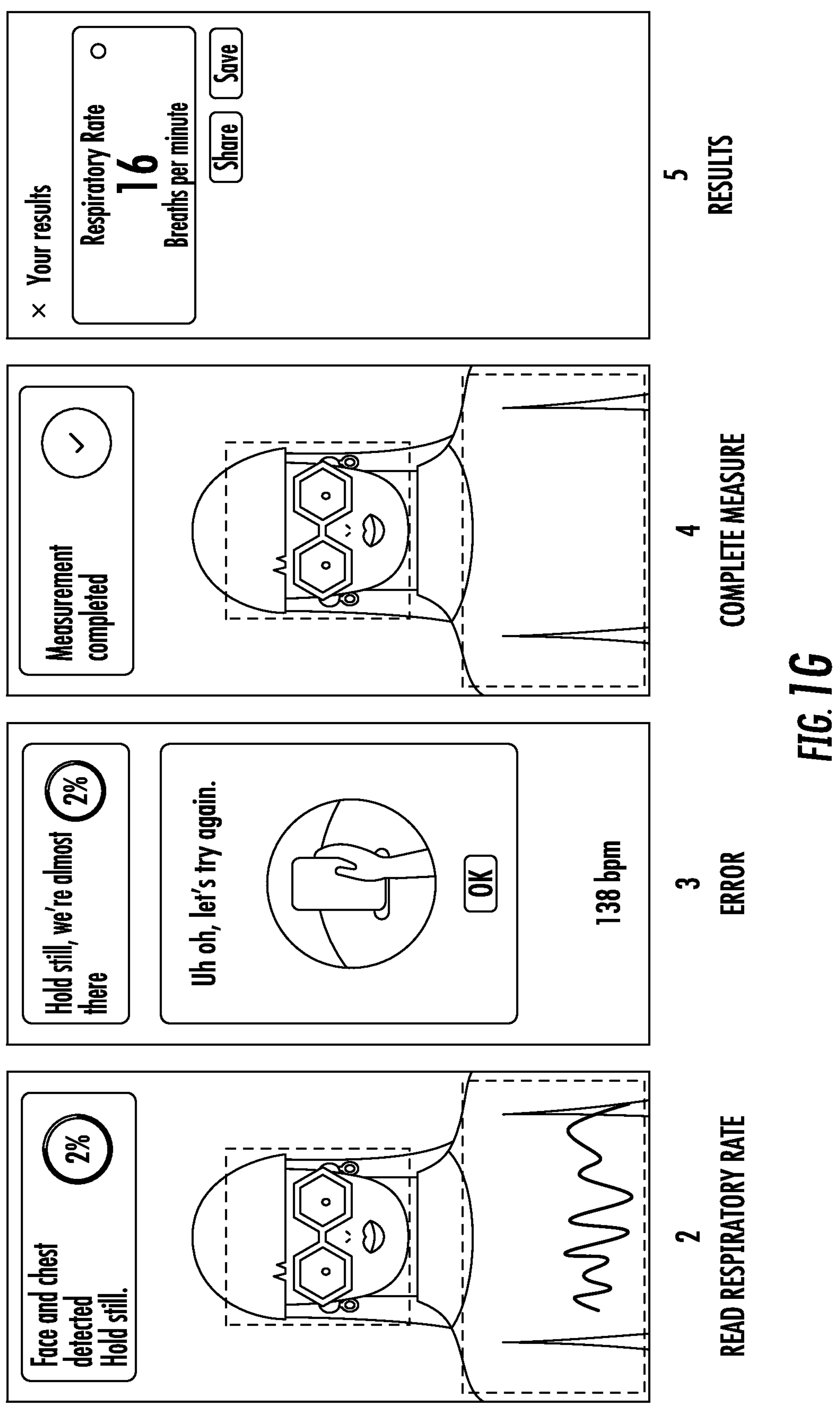
Figure 1H:
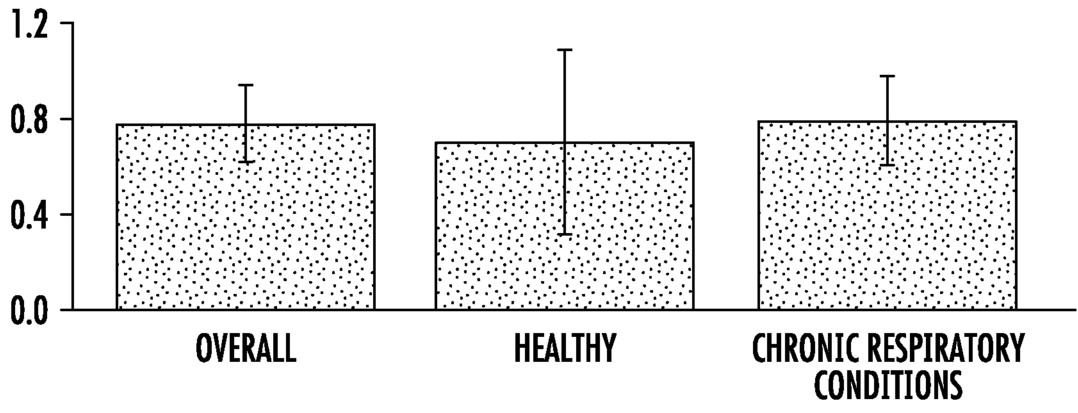
FIG. 1H shows the measurements/results for mean absolute error (MAE) for RR according to example embodiments of the present disclosure.

FIG. 1E shows an example "setup" of how measurements are taken using a video of the participant (e.g. a set of image frames captured at a series of corresponding times) via the front-facing camera. FIGS. 1F-G show example user interfaces for guiding a user to perform the RR evaluation. Following an onboarding process of FIG. 1F, a plurality of image frames at a series of respective times, e.g. video frames, are captured. The first diagram of FIG. 1G shows the display on a screen of user device at a moment during this process, and the fourth shows a display of the result. FIG. 1H shows the measurements/results for mean absolute error (MAE) for RR.

Example Algorithm Description

An example contactless method proposed herein can estimate RR by performing motion analysis in a ROI of the video stream that includes the base of the neck, shoulder line and upper torso of the participant. One challenge is that variations in video due to respiratory motions are hard to distinguish from noise. The proposed techniques can use Eulerian, phase-based motion processing that is particularly suited for analyzing subtle motions. In each video frame, the position at each pixel of one or more pixels in the frame can be represented by the phase of spatially localized sinusoids in multiple scales (frequencies).

In some examples, the phase-based motion analysis can amplify small motions by modifying local phase variations in a complex steerable pyramid representation of the video. For example, a computing system can compute the local phase over time at every spatial scale and orientation of a steerable pyramid. Then, the computing system can temporally bandpass these phases to isolate specific temporal frequencies relevant to a given application and remove any temporal DC component. These temporally bandpassed phases can correspond to motion in different spatial scales and orientations. To synthesize magnified motion, the computing system can multiply the bandpassed phases by an amplification factor. These amplified phase differences can then be used magnify the motion in the sequence by modifying the phases of each coefficient by this amount for each frame.

As an example, in some implementations, the position can be determined using Riesz pyramids as described in Wadhwa et al., Riesz pyramids for fast phase-based video magnification. 2014 IEEE International Conference on Computational Photography (ICCP). Published online 2014. doi: 10.1109/iccphot.2014.6831820. Additional example techniques that can be used are described in: Wadhwa et al., Phase-based video motion processing, ACM Transactions on Graphics, Volume 32, Issue 4, July 2013, Article No.: 80, pp 1-10; and Wadhwa et al., Eulerian Video Magnification and Analysis, Communications of the ACM, January 2017, Vol. 60 No. 1, Pages 87-95.

Referring again to the proposed algorithm, to aggregate the information across scales and to obtain an intuitive representation of motion, the spatial phases can then be transformed into optical flow by linearly approximating the position implied by each phase coefficient and averaging across scales. Using the Halide high-performance image library, the phase and optical flow computation can be sped up to achieve real-time processing (1-4 ms per frame on Pixel 3a and Pixel 4 mobile devices).

Ensembling can then be used to improve the predictive performance. A spectral-spatial ensemble can be built in the following way. The respiratory ROI, together with the four quadrants obtained by equally subdividing the ROI into five (or any other plural number) defined regions, over each of which the vertical component of the optical flow (e.g. the component parallel to a "vertical" direction which may be defined as parallel to one of the sides of the image frames, typically a direction in which the torso is spaced from the head) can be averaged. This can result in five respiratory waveforms. Next, frequency-domain representations for each of these respiratory waveforms can be computed via FFT, from which power spectra can be computed. The power spectra can then be aggregated to obtain a final ensembled power spectrum. Bandpass-filtering can be performed, e.g. based on respective high and/or low frequency thresholds, to remove low and/or high frequencies unlikely to represent valid RRs. Example filter cut-off frequencies (thresholds) corresponded to a low of 6 breaths/min and a high of 60 breaths/min. The maximum power frequency and the corresponding SNR value can be computed from the ensembled power spectrum. The waveform corresponding to the entire ROI can be used for displaying the breathing pattern to the user in the mobile app.

In certain situations there may be insufficient periodicity in the respiratory waveform (e.g., the participant briefly held their breath or changed their respiratory rate within the time window used for analyzing the waveform). To increase the robustness of RR estimation, the algorithm can fall back on a time domain estimation method based on counting zero crossings of the waveform corresponding to the entire ROI whenever the SNR obtained via the FFT-based method is lower than a certain threshold. Two versions of the algorithm were tested, differing only in terms of this threshold: SNR<−6.0 dB ("version A") and SNR<−4.0 dB ("version B"). The higher value for the threshold in version B invoked the time domain estimation method more often, which was hypothesized to improve accuracy by improving robustness to irregular breathing.

Example Study Design and Participants

An example prospective observational clinical validation study was performed to assess the accuracy of the study algorithm in measuring the RR in healthy adults and patients with chronic respiratory conditions. Chronic respiratory conditions included moderate or severe chronic obstructive pulmonary disease (COPD) and asthma that was not well-controlled based on specific study criteria. Also, participants with significant tremor were excluded.

Example Data Collection

Each participant underwent 30 seconds of data collection using a Pixel 4 smartphone running Android 10 (Google LLC, Mountain View, CA). The two algorithm versions (A and B) were tested sequentially. The participants followed the study protocol via instructions from the study app, without intervention from the study staff. Participants were prompted to prop the study phone on a table using provided common household items, such that the upper body was centered in the video capture (see, e.g., FIGS. 1E-G). There were no specific requirements on the type of clothing worn during the study or additional custom lighting equipment. The in-app instructions guided the participants to wait several minutes after any active movement and to stay comfortable and breathe normally during the measurements.

During the data collection, RR was manually counted and recorded by two research coordinators. The two observers counted the number of breaths independently and blinded to the algorithm-estimated results. The agreement between the two measurements was high (Pearson correlation coefficient: 0.962; mean difference: 0.48±0.88 breaths/min; range, 0-4). The mean of the two human-measured RRs, rounded off to the nearest integer, was taken to be the reference RR.

Example Statistical Analysis and Sample Size Calculations

Each participant contributed a single pair of measurements for each algorithm version, and the MAE was used as the primary evaluation metric. The study hypothesis was that MAE would be <3 breaths/min. One-sample t-tests were done to determine whether the MAE was statistically significantly <3 breaths/min. A pre-specified subgroup analysis was also performed, stratified by history of chronic respiratory conditions. In addition, post-hoc subgroup analyses were performed for age and race/ethnicity subgroups.

Bland-Altman plots were used to analyze further for any trends in errors. Differences between the two algorithm versions were compared using a paired t-test.

To estimate the sample size required for the study, an IRB-approved feasibility study with 80 healthy adults was conducted. Based on that MAE±standard deviation (0.96±0.72 breaths/min), a sample size of 50 participants was estimated to provide a power of >0.99 to detect an MAE <3. The power was also >0.99 for both the subgroup of 10 healthy participants and the subgroup of 40 with chronic respiratory conditions. If the MAE and standard deviation were doubled, the power would be >0.99, 0.71, and >0.99, respectively, for the full sample, healthy participants, and those with chronic respiratory conditions.

Example Results

A total of 50 participants were enrolled in the RR study, including 10 healthy participants and 40 participants with chronic respiratory conditions. Participants had diverse demographic characteristics. The average reference RR was 15.3±3.7 breaths/min.

Both versions of the example algorithm successfully estimated RR in all of the study subjects; thus, all of the 50 study participants contributed to the final analysis. The MAE in the overall study population was 0.84±0.97 and 0.78±0.61 breaths/min for algorithm versions A and B, respectively, which were significantly lower than the pre-specified threshold of 3 breaths/min ($p<0.001$ for both). Each subgroup also showed MAE values significantly lower than the threshold: algorithm version A, 0.60±0.52 breaths/min ($p<0.001$) for the healthy cohort and 0.90±1.05 breaths/min ($p<0.001$) for the cohort with chronic respiratory conditions; algorithm version B, 0.70±0.67 breaths/min ($p<0.001$) and 0.80±0.60 breaths/min ($p<0.001$), respectively. No significant variations across age and race subgroups were seen.

Example Discussion

Thus, the present disclosure provides the results of two example prospective clinical studies validating the performance of example smartphone algorithms to estimate HR and RR. Both example algorithms showed high accuracy compared to the reference standard vital sign measurements, with HR within 5% and RR within 3 breaths/min (the pre-specified targets). In addition, the HR estimation was robust across skin tones, and the RR estimation generalized to participants with common chronic respiratory conditions, COPD, and asthma.

The accuracy of the HR algorithm is especially notable. A MAE less than 5 beats/min or a MAPE less than 10% are standard accuracy thresholds for HR monitors. The MAE of 1.32 beats/min in HR is lower than that reported for contemporary wearable devices (4.4 to 10.2 beats/min at rest), albeit with several differences in study design and population. The MAPE of 1.63% is comparable to the performance of current wearable devices. For example, Shcherbina et al. tested six wrist worn devices to show a median error <5% for all across various activities and a median error of 2.0% for the best-performing device. Because skin tone can be a potential source of bias in medical devices, and the accuracy of PPG-based HR estimation can be affected by melanin's light-absorbing property, participants with diverse skin tones were enrolled to validate the robustness of the example HR estimation algorithm across skin tones.

For consumer-grade RR monitoring devices, there is no well-accepted accuracy standard. The MAE of 0.78 breaths/min attained in the study is comparable to that of professional healthcare devices, which have reported accuracy of ±2-3 breaths/min. This could be a helpful reference point for future studies. In this study, two example algorithm versions for RR estimation were studied that differed only in the SNR threshold. The results suggest that this parameter had little impact on the accuracy or error rates.

This work supports the use of consumer-grade smartphones for measuring HR and RR. One application of these measurements is in fitness and wellness for the general consumer user. Specifically, an elevated resting HR or slower heart rate recovery after exercise has been linked to lower physical fitness and higher risk of all-cause mortality. Evidence suggests use of direct-to-consumer mobile health technologies may enhance positive lifestyle modification such as increased physical activity, more weight loss, and better diabetes control. Tracking one's own health-related parameters over time by the general public can potentially increase motivation for a healthier lifestyle by providing an objective, quantifiable metric. Additionally, there exists strong evidence that regular physical activity is key to improving one's health independent of demographics or current fitness level for maintaining cardiovascular health. Monitoring one's HR is also an easy and effective way to assess and adjust exercise intensity or enable smartphone-based measurement of cardiorespiratory fitness.

With further clinical validation across broad populations, such smartphone-based measurement could also be useful in various settings, most notably telehealth where vital sign measurement is challenging due to the remote nature of the patient encounter. Though patients can in principle count their own HR or RR, this can be error prone due to factors such as biases that acute awareness of the self-examination can cause. Because the demand for remote triage, diagnosis and monitoring is increasing, there is increased attention being paid to accurate remote physical examination.

Example Telemedicine Configurations

Figure 2A:
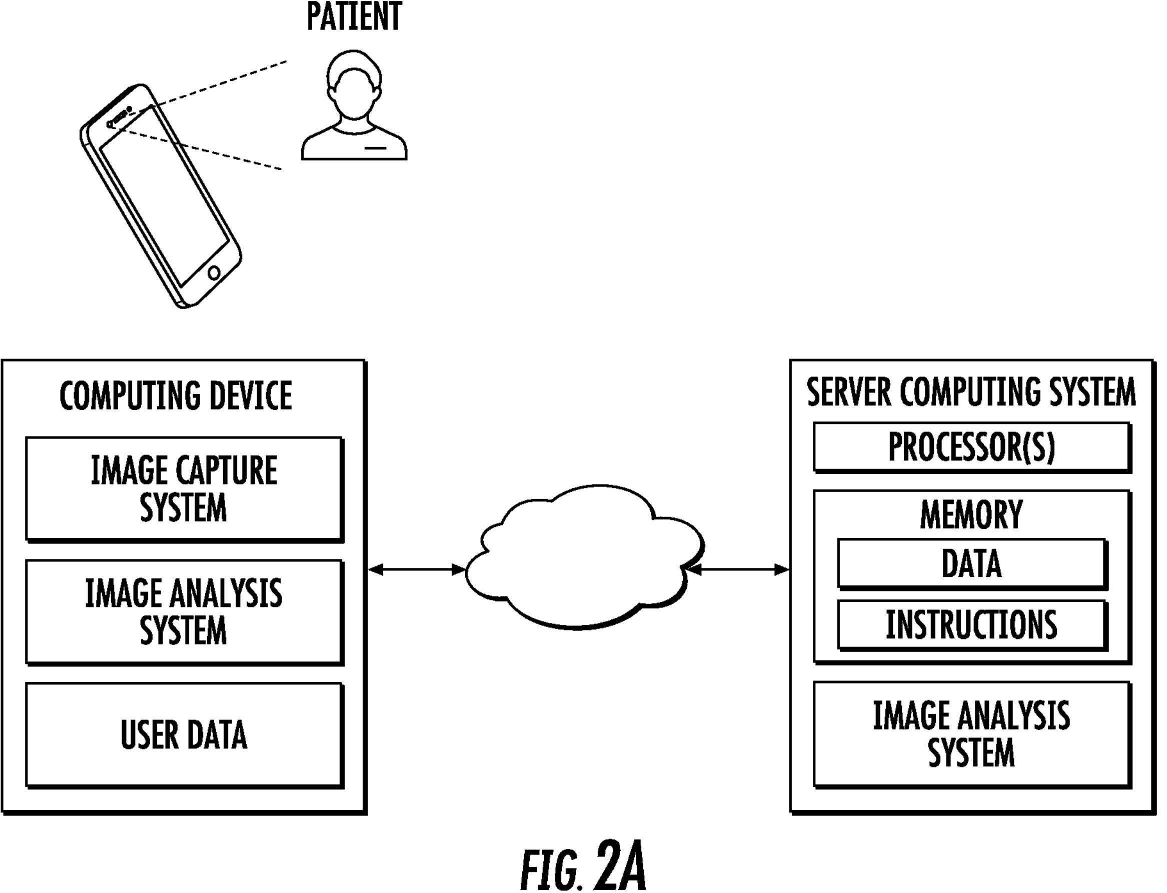
FIG. 2A depicts an example block diagram of a system for analyzing imagery according to example embodiments of the present disclosure.

FIG. 2A depicts an example client-server environment according to example embodiments of the present disclosure. Specifically, FIG. 2A depicts a user computing device and a server system that communicate over a network. The computing device can be a personal electronic device such as a smartphone, tablet, laptop, and so on. The computing device can include an image capture system, at least a portion of an image analysis system, and user data. The image capture system can capture one or more images of a patient. The image analysis system can determine a heart rate and/or a respiratory rate according to any of the techniques described herein.

In some implementations, the computing device can transmit the captured image(s) to the server computing device. Alternatively or additionally, the image analysis system can generate intermediate data for or from one or more images. In this way, the computing device can transmit intermediate data representing the image, rather than the image itself. This can reduce the amount of bandwidth needed to transmit the images to the server computing system.

The user data can be stored in a local data storage device and can include user clinical data, user demographic data, and/or user medical history data. This information can be transmitted to the server computing system as needed with user permission. In some examples, the image analysis system at the user computing device can include a context component that generates a feature representation for the user data. In some examples, the image analysis system can combine one or more image intermediate data and the feature representation data for the user data.

The server computing system can include some or all of an image analysis system. The image analysis system can determine a heart rate and/or a respiratory rate according to any of the techniques described herein.

For example, the server computing system can receive one or more of: image data, one or more intermediate data generated from the image data, user data, or other forms of data. Any and/or all of these types of data can be received at the server computing system and used to generate one or more output such as image analyses (e.g., heart rate and/or respiratory rate) and/or other physical assessment predictions. The image analysis system outputs can be transmitted to the computing device or to another third-party device as needed and approved by the user.

Figure 2B:
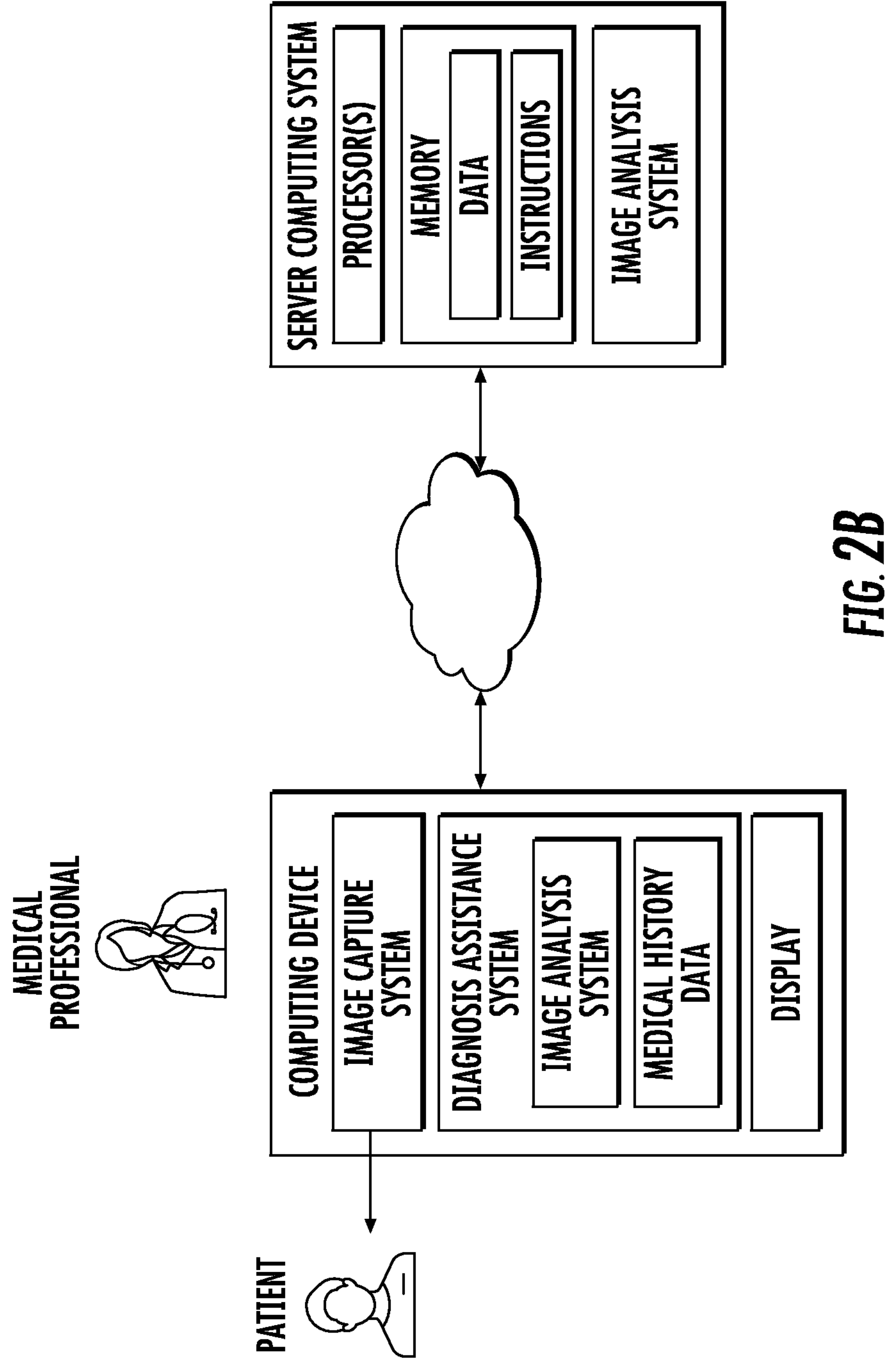
FIG. 2B depicts an example block diagram of a system for analyzing imagery according to example embodiments of the present disclosure.

FIG. 2B depicts an example block diagram of a system for providing physical assessment assistance according to example embodiments of the present disclosure. In this example, the computing device is associated with a medical professional (e.g., a doctor (e.g., optometrist, ophthalmologist, radiologist, dermatologist, etc.), a nurse practitioner, and so on). The medical professional can utilize the computing device to obtain aid during their physical assessment process. The computing device can include an image capture system (e.g., a camera and associated software), a physical assessment assistance system, and a display. The physical assessment assistance system can include some or all of an image analysis system and medical history data.

The medical professional can use the computing device to capture one or more images of the patient using the image capture system. The physical assessment assistance system can process the imagery locally, generate intermediate data locally, or transmit the raw image data to the server computing system. Similarly, medical history data can be processed locally to generate a feature representation or transmitted to the server computing system. In some examples, the physical assessment assistance system includes the full image analysis system and thus can generate image analyses without transmitting data to the server computing system.

In some examples, the physical assessment assistance system transmits data to the server computing system. The image analysis system at the server computing system can generate one or more outputs such as image analyses or other physical assessment predictions and transmit the data back to the physical assessment assistance system for display to the medical professional in the display at the computing device.

Figure 2C:
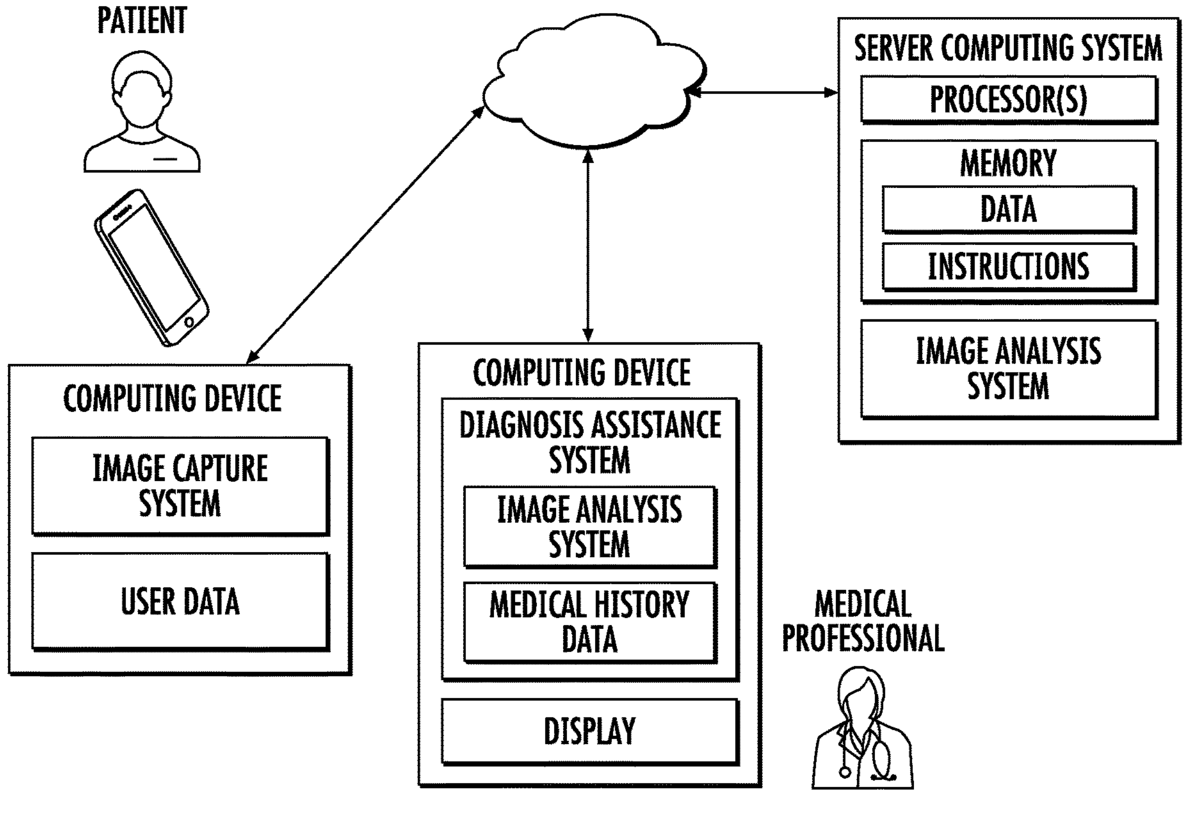
FIG. 2C depicts an example block diagram of a system for analyzing imagery according to example embodiments of the present disclosure.

FIG. 2C depicts an example block diagram of a system for providing physical assessment assistance according to example embodiments of the present disclosure. In this example, the patient is not physically present with the medical professional. Instead, the patient uses a computing device with an image capture system to transmit one or more images (and potentially user data) to the computing device associated with the medical professional and/or the server computing system via a network. Once the computing device receives the one or more images from the computing device associated with the patient, the process can proceed as described above with respect to FIG. 2A or 2B. The medical professional can then transmit any relevant outputs such as physical assessment information to the computing device of the patient.

Example Devices and Systems

Figure 3:
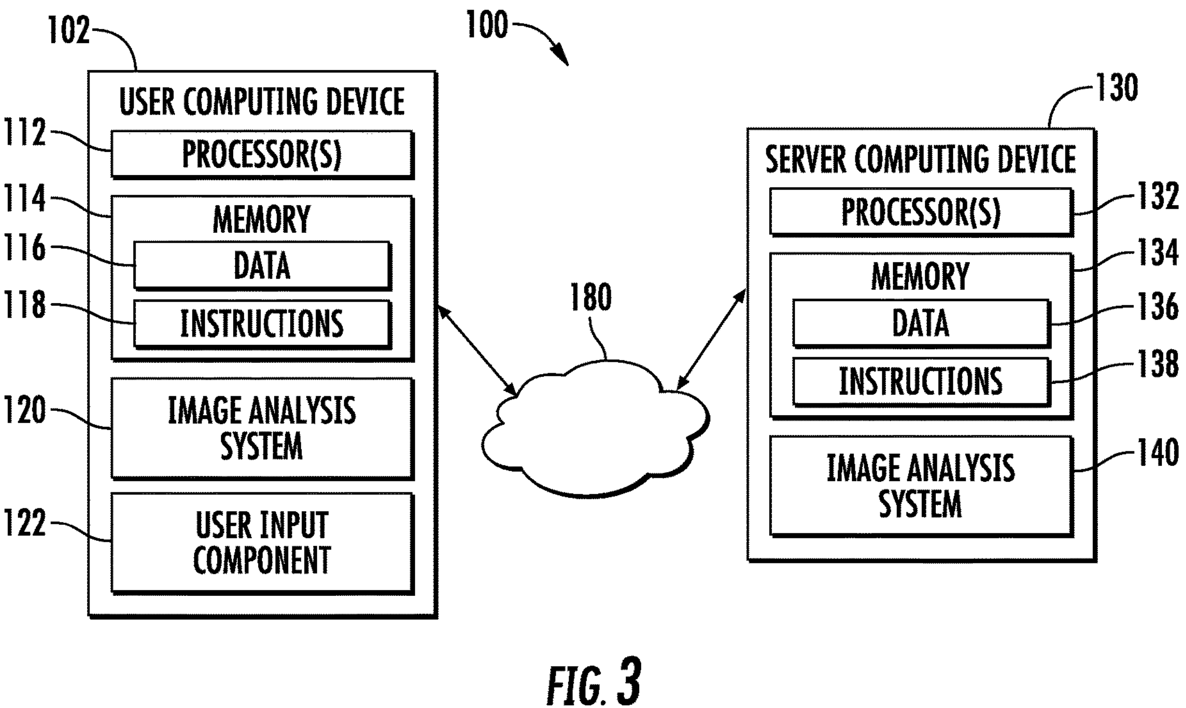
FIG. 3 depicts a block diagram of an example computing system according to example embodiments of the present disclosure.

FIG. 3 depicts a block diagram of an example computing system 100 according to example embodiments of the present disclosure. The system 100 includes a user computing device 102 and a server computing system 130 that are communicatively coupled over a network 180.

The user computing device 102 can be any type of computing device, such as, for example, a personal computing device (e.g., laptop or desktop), a mobile computing device (e.g., smartphone or tablet), a gaming console or controller, a wearable computing device, an embedded computing device, or any other type of computing device.

The user computing device 102 includes one or more processors 112 and a memory 114. The one or more processors 112 can be any suitable processing device (e.g., a processor core, a microprocessor, an ASIC, an FPGA, a controller, a microcontroller, etc.) and can be one processor or a plurality of processors that are operatively connected. The memory 114 can include one or more non-transitory computer-readable storage media, such as RAM, ROM, EEPROM, EPROM, flash memory devices, magnetic disks, etc., and combinations thereof. The memory 114 can store data 116 and instructions 118 which are executed by the processor 112 to cause the user computing device 102 to perform operations.

In some implementations, the user computing device 102 can store or include one or more image analysis systems 120 (e.g. software program(s)). For example, the image analysis systems 120 can be or can otherwise include various image analysis systems such as heart rate determination systems and/or respiratory rate determination systems. The systems 120 can implement any of the methods described herein.

In some implementations, the one or more image analysis systems 120 can be received from the server computing system 130 over network 180, stored in the user computing device memory 114, and then used or otherwise implemented by the one or more processors 112. In some implementations, the user computing device 102 can implement multiple parallel instances of a single image analysis system 120 (e.g., to perform parallel image analysis across multiple instances of imagery).

Additionally or alternatively, one or more image analysis systems 140 can be included in or otherwise stored and implemented by the server computing system 130 that communicates with the user computing device 102 according to a client-server relationship. For example, the image analysis systems 140 can be implemented by the server computing system 140 as a portion of a web service (e.g., a physical assessment service).

The user computing device 102 can also include one or more user input components 122 that receives user input. For example, the user input component 122 can be a touch-sensitive component (e.g., a touch-sensitive display screen or a touch pad) that is sensitive to the touch of a user input object (e.g., a finger or a stylus). The touch-sensitive component can serve to implement a virtual keyboard. Other example user input components include a microphone, a traditional keyboard, a camera, or other means by which a user can provide user input.

The server computing system 130 includes one or more processors 132 and a memory 134. The one or more processors 132 can be any suitable processing device (e.g., a processor core, a microprocessor, an ASIC, an FPGA, a controller, a microcontroller, etc.) and can be one processor or a plurality of processors that are operatively connected. The memory 134 can include one or more non-transitory computer-readable storage media, such as RAM, ROM, EEPROM, EPROM, flash memory devices, magnetic disks, etc., and combinations thereof. The memory 134 can store data 136 and instructions 138 which are executed by the processor 132 to cause the server computing system 130 to perform operations.

In some implementations, the server computing system 130 includes or is otherwise implemented by one or more server computing devices. In instances in which the server computing system 130 includes plural server computing devices, such server computing devices can operate according to sequential computing architectures, parallel computing architectures, or some combination thereof.

As described above, the server computing system 130 can store or otherwise include one or more image analysis systems 140. For example, the image analysis systems 140 can be or can otherwise include various image analysis systems such as heart rate determination systems and/or respiratory rate determination systems. The systems 140 can implement any of the methods described herein.

The network 180 can be any type of communications network, such as a local area network (e.g., intranet), wide area network (e.g., Internet), or some combination thereof and can include any number of wired or wireless links. In general, communication over the network 180 can be carried via any type of wired and/or wireless connection, using a wide variety of communication protocols (e.g., TCP/IP, HTTP, SMTP, FTP), encodings or formats (e.g., HTML, XML), and/or protection schemes (e.g., VPN, secure HTTP, SSL).

FIG. 3 illustrates one example computing system that can be used to implement the present disclosure. Other computing systems can be used as well.

Example Methods

Figure 4:
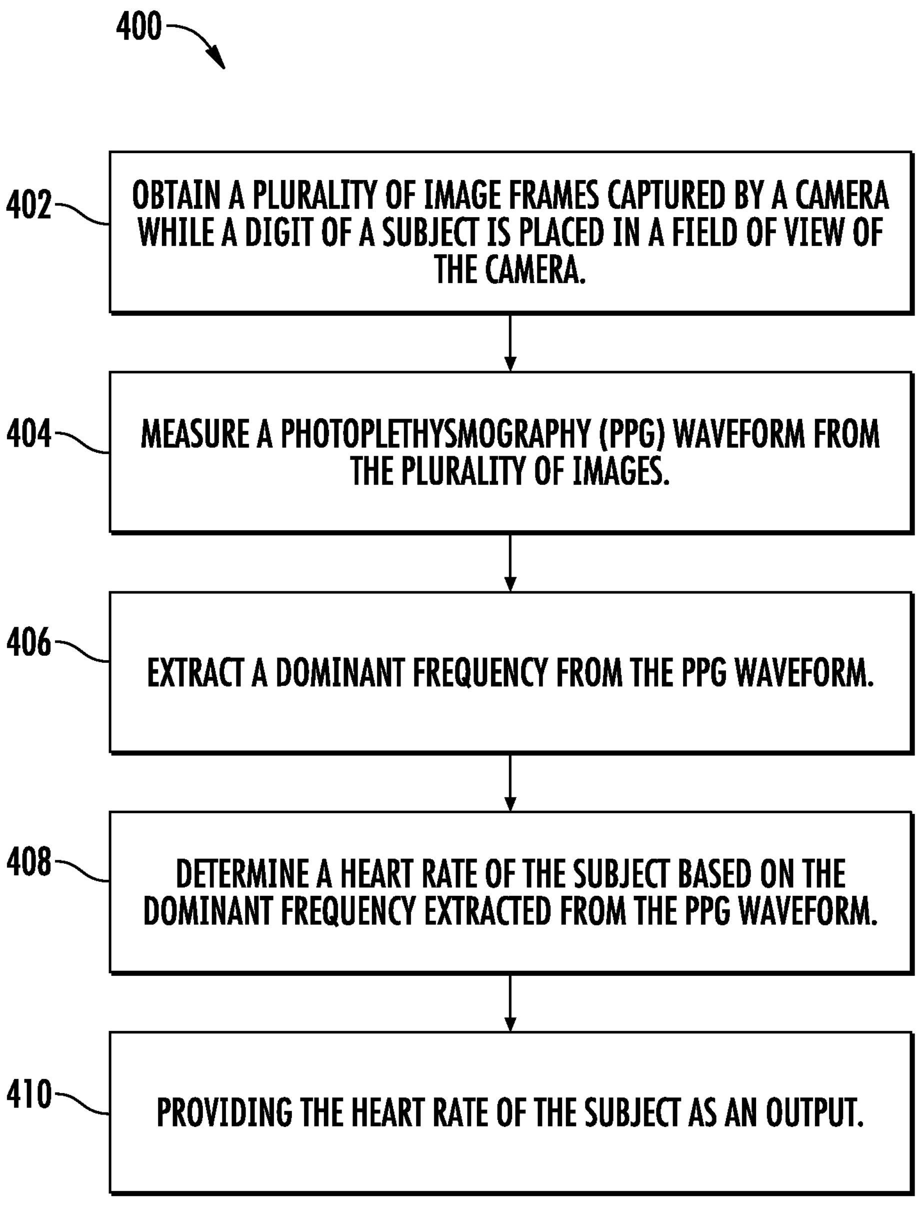
FIG. 4 depicts a flow chart diagram of an example method to measure heart rate according to example embodiments of the present disclosure.

FIG. 4 depicts a flow chart diagram of an example method to measure heart rate according to example embodiments of the present disclosure. Although FIG. 4 depicts steps performed in a particular order for purposes of illustration and discussion, the methods of the present disclosure are not limited to the particularly illustrated order or arrangement. The various steps of the method 400 can be omitted, rearranged, combined, and/or adapted in various ways without deviating from the scope of the present disclosure.

At 402, the method 400 includes obtaining, by a computing system comprising one or more computing devices, a plurality of image frames captured by a camera while a digit of the subject is placed in a field of view of the camera. For example, the digit can be a finger. As an example, the digit of the subject can be placed in physical contact with an outermost lens or cover of the camera during capture of the plurality of image frames. Alternatively, the digit of the subject can be adjacent to, but not in physical contact, with the outermost lens or cover of the camera.

At 404, the method 400 includes measuring, by the computing system, a photoplethysmography (PPG) waveform from the plurality of image frames. In some implementations, measuring, by the computing system, the PPG waveform from the plurality of image frames can include selecting, by the computing system, regions of interest (ROIs) from the plurality of image frames; averaging, by the computing system, pixels in each of the regions of interest on a per-channel basis to form a plurality of per-channel waveforms; and computing, by the computing system, the PPG waveform as a weighted average of the plurality of per-channel waveforms. As examples, the ROIs can be manually or automatically selected. As one example, the ROIs can include an entirety of the frame and each of the four quadrants of the frame. As another example, the ROIs can include a top half, a bottom half, a left half, and a right half. As another example, the ROIs can include a bounding box associated with a digit. For example, each of the ROIs may be defined as a respective portion of the bounding box (e.g. a top half, a bottom half, a left half, and a right half), or a respective bounding box. In some implementations, the bounding box(es) can be generated by an object detection model provided with the frame as input. As examples, the channels of the frame can include color channels in a color space such as red, green, and blue channels in an RGB color space.

In some implementations, measuring the PPG waveform can also include applying, by the computing system, one or more bandpass filters to the PPG waveform. As examples, filter cut-off frequencies can correspond to a low of 30 beats/min and high of 360 beats/min.

In some implementations, measuring the PPG waveform can also include smoothing, by the computing system, the PPG waveform using a maximum allowed change in amplitude which is a function of a moving average of PPG waveform values. As an example, large amplitude changes in PPGs due to motion can be suppressed by limiting maximum allowed changes in amplitudes as 3× of moving average values.

At 406, the method 400 includes extracting, by the computing system, a dominant frequency from the PPG waveform.

In some implementations, extracting, by the computing system, the dominant frequency from the PPG waveform can include: generating, by the computing system, a Fast Fourier Transform representation of the PPG waveform; and extracting, by the computing system, the dominant frequency from the Fast Fourier Transform representation. For example, extracting, by the computing system, the dominant frequency from the Fast Fourier Transform representation can include summing, by the computing system, powers of first, second, and third harmonics.

In some implementations, extracting, by the computing system, the dominant frequency from the PPG waveform can include: determining, by the computing system, a signal to noise ratio for each region of interest by computing a ratio between a power of a dominant frequency and powers of non-dominant frequencies on a logarithmic scale; identifying, by the computing system, the region of interest with the largest signal to noise ratio; and extracting, by the computing system, the dominant frequency of the region of interest with the largest signal to noise ratio.

At 408, the method 400 includes determining, by the computing system, a heart rate of the subject based on the dominant frequency extracted from the PPG waveform. For example, the heart rate of the subject can be set equal to the dominant frequency extracted from the PPG waveform expressed in the format of beats per minute.

At 410, the method 400 includes providing, by the computing system, the heart rate of the subject as an output. As examples, providing the heart rate as an output can include storing data representing the heart rate of the subject in a memory, providing data representing the heart rate of the subject for display (e.g., to the subject or a medical provider), and/or transmitting data representing the heart rate of the subject over a communications network.

Figure 5:
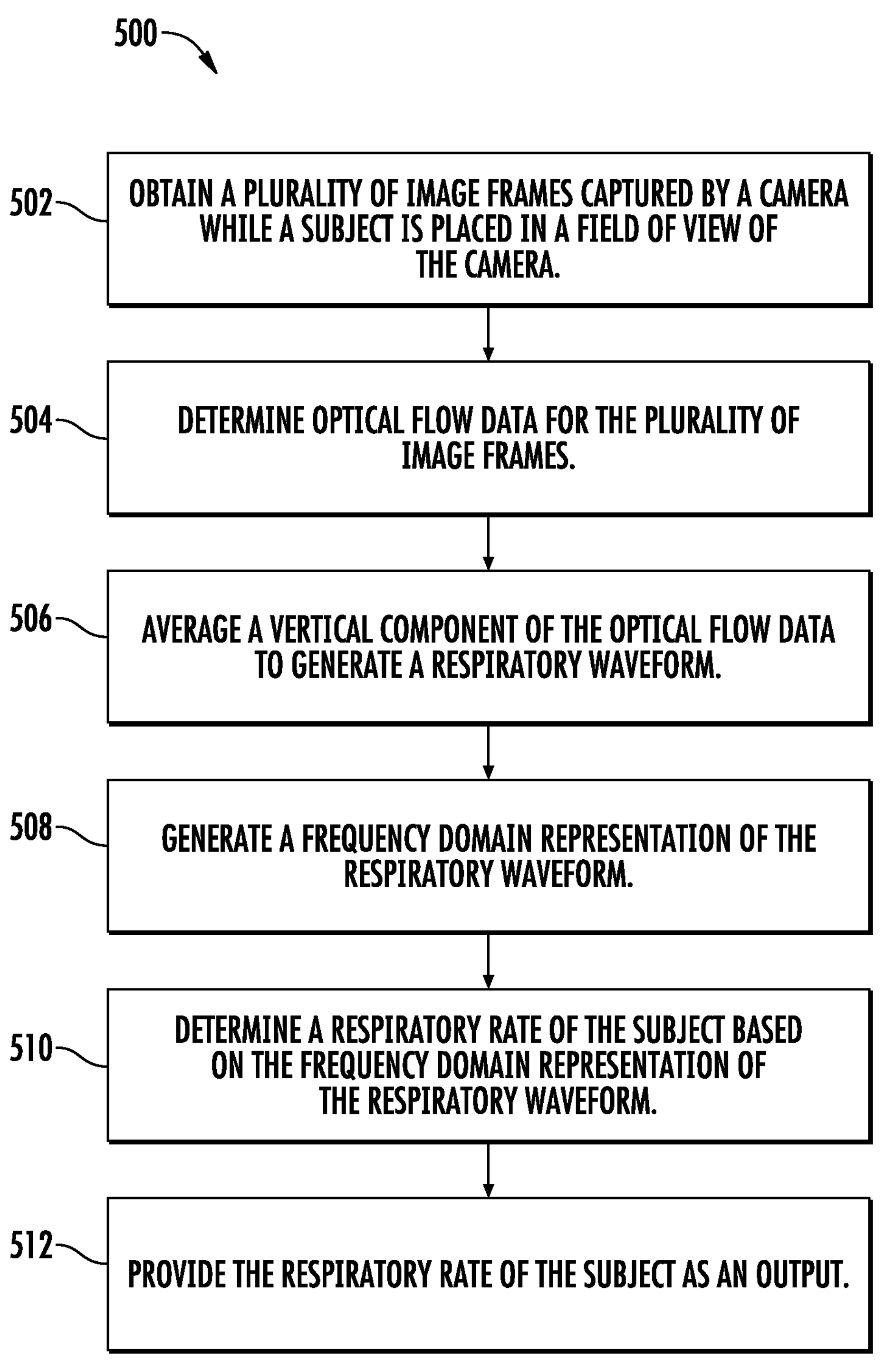
FIG. 5 depicts a flow chart diagram of an example method to measure respiratory rate according to example embodiments of the present disclosure.

FIG. 5 depicts a flow chart diagram of an example method to measure respiratory rate according to example embodiments of the present disclosure. Although FIG. 5 depicts steps performed in a particular order for purposes of illustration and discussion, the methods of the present disclosure are not limited to the particularly illustrated order or arrangement. The various steps of the method 500 can be omitted, rearranged, combined, and/or adapted in various ways without deviating from the scope of the present disclosure.

At 502, the method 500 includes obtaining, by a computing system comprising one or more computing devices, a plurality of image frames captured by a camera while a subject is placed in a field of view of the camera. For example, a base of a neck, a shoulder line, and/or an upper torso of the subject can be depicted by the plurality of image frames.

At 504, the method 500 includes determining, by the computing system, optical flow data for the plurality of image frames.

In some implementations, determining, by the computing system, optical flow data for the plurality of image frames can include: performing, by the computing system, a Eulerian phase-based motion analysis on the plurality of image frames to generate phase-based motion data; and generating, by the computing system, the optical flow data for the plurality of image frames based on the phase-based motion data.

As one example, determining the optical flow data can include determining, by the computing system, for each pixel of one or more pixels in each frame, a position represented by a phase of spatially localized sinusoids in multiple scales; and transforming, by the computing system, the phase of spatially localized sinusoids into optical flow data by linearly approximating the position implied by each phase coefficient and averaging across scales.

At 506, the method 500 includes averaging, by the computing system, a vertical component of the optical flow data to generate a respiratory waveform.

At 508, the method 500 includes generating, by the computing system, a frequency domain representation of the respiratory waveform.

At 510, the method 500 includes determining, by the computing system, the respiratory rate of the subject based on the frequency domain representation of the respiratory waveform.

In some implementations, steps 506, 508, and/or 510 can be performed for each of a plurality of regions of interest (ROIs). Thus, in some implementations, the method 500 can include selecting, by the computing system, a plurality of regions of interest; averaging, by the computing system, a vertical component of the optical flow data for each of the regions of interest to generate a plurality of respiratory waveforms respectively for the plurality of regions of interest; and determining, by the computing system, the respiratory rate of the subject based on the plurality of respiratory waveforms. As examples, the ROIs can be manually or automatically selected. As one example, the ROIs can include an entirety of the frame and each of the four quadrants of the frame. As another example, the ROIs can include a top half, a bottom half, a left half, and a right half. As another example, the ROIs can include one or more bounding boxes associated with a body, a neck, a shoulder line, and/or an upper torso of the subject. In some implementations, the bounding box(es) can be generated by an object detection model provided with the frame as input.

Referring still to FIG. 5, at 510, determining, by the computing system, the respiratory rate of the subject based on the one or more waveforms can include: generating, by the computing system, a power spectrum from a frequency domain representation of each respiratory waveform; aggregating, by the computing system, the power spectra for the one or more respiratory waveforms to obtain a final ensembled power spectrum; and determining, by the computing system, the respiratory rate of the subject based on a maximum power frequency of the final ensembled power spectrum.

As an example, bandpass-filtering can be performed to remove low and high frequencies unlikely to represent valid RRs. Example filter cut-off frequencies include a low of 6 breaths/min and a high of 60 breaths/min. The maximum power frequency and the corresponding SNR value can be computed from the ensembled power spectrum. The waveform corresponding to the entire ROI can be used for displaying the breathing pattern to the user in the mobile app.

At 512, the method 500 includes providing, by the computing system, the respiratory rate of the subject as an output. As examples, providing the respiratory rate as an output can include storing data representing the respiratory rate of the subject in a memory, providing data representing the respiratory rate of the subject for display (e.g., to the subject or a medical provider), and/or transmitting data representing the respiratory rate of the subject over a communications network.

In some implementations, the method 500 can include defaulting, by the computing system, to a time-domain estimation of the respiratory waveform when a signal to noise ratio associated with the frequency domain representation falls below a threshold.

Additional Disclosure

The technology discussed herein makes reference to servers, databases, software applications, and other computer-based systems, as well as actions taken and information sent to and from such systems. The inherent flexibility of computer-based systems allows for a great variety of possible configurations, combinations, and divisions of tasks and functionality between and among components. For instance, processes discussed herein can be implemented using a single device or component or multiple devices or components working in combination. Databases and applications can be implemented on a single system or distributed across multiple systems. Distributed components can operate sequentially or in parallel.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one of ordinary skill in the art. For instance, features illustrated or described as part of one embodiment can be used with another embodiment to yield a still further embodiment. Thus, it is intended that the present disclosure cover such alterations, variations, and equivalents.

What is claimed is:

1. A computer-implemented method to measure heart rate of a subject, the method comprising:

obtaining, by a computing system comprising one or more computing devices, a plurality of image frames captured by a camera while a digit of the subject is placed in a field of view of the camera;

measuring, by the computing system, a plurality of photoplethysmography (PPG) waveforms extracted from the plurality of image frames;

wherein the plurality of PPG waveforms are measured to identify a particular PPG waveform with the greatest signal to noise ratio;

extracting, by the computing system, a dominant frequency from the particular PPG waveform; and determining, by the computing system, the heart rate of the subject based on the dominant frequency extracted from the particular PPG waveform.

2. The computer-implemented method of claim 1, wherein measuring, by the computing system, the plurality of PPG waveforms from the plurality of image frames comprises:

selecting, by the computing system, regions of interest from the plurality of image frames;

averaging, by the computing system, pixels in each of the regions of interest on a per-channel basis to form a plurality of per-channel waveforms for each region of interest; and computing, by the computing system, one of the plurality of PPG waveforms for each region of interest as a weighted average of the plurality of per-channel waveforms for that region of interest.

3. The computer-implemented method of claim 1, wherein measuring each of the plurality of PPG waveforms comprises:

applying, by the computing system, one or more bandpass filters to the PPG waveform.

4. The computer-implemented method of claim 1, wherein measuring each of the plurality of PPG waveforms comprises:

smoothing, by the computing system, the PPG waveform using a maximum allowed change in amplitude which is a function of a moving average of PPG waveform values.

5. The computer-implemented method of claim 1, wherein extracting, by the computing system, the dominant frequency from the particular PPG waveform comprises:

generating, by the computing system, a Fast Fourier Transform representation of the PPG waveform; and extracting, by the computing system, the dominant frequency from the Fast Fourier Transform representation.

6. The computer-implemented method of claim 5, wherein extracting, by the computing system, the dominant frequency from the Fast Fourier Transform representation comprises:

summing, by the computing system, powers of first, second, and third harmonics.

7. The computer-implemented method of claim 1, wherein extracting, by the computing system, the dominant frequency from the particular PPG waveform comprises:

determining, by the computing system, a signal to noise ratio for each region of interest by computing a ratio between a power of a dominant frequency and powers of non-dominant frequencies on a logarithmic scale;

identifying, by the computing system, the region of interest with the largest signal to noise ratio; and extracting, by the computing system, the dominant frequency of the region of interest with the largest signal to noise ratio.

8. The computer-implemented method of claim 1, wherein the digit comprises a finger.

9. The computer-implemented method of claim 1, wherein the digit of the subject is in physical contact with an outermost lens or cover of the camera during capture of the plurality of image frames.

10. A computing device comprising:

a camera;

one or more processors; and one or more non-transitory computer-readable media that collectively store instructions that, when executed by the one or more processors, cause the computing device to perform the method of claim 1.

11. One or more non-transitory computer-readable media that collectively store instructions that, when executed by one or more processors, cause a computing device to perform the method of claim 1.

12. A computer system, comprising:

one or more processors; and one or more non-transitory computer readable media that collectively store instructions that, when executed by the one or more processors, cause the computing system to perform operations, the operations comprising:

obtaining a plurality of image frames captured by a camera while a digit of the subject is placed in a field of view of the camera;

measuring a plurality of photoplethysmography (PPG) waveforms respectively extracted from a plurality of regions of interest defined relative to the plurality of image frames to identify a particular PPG waveform with the greatest signal-to-noise-ratio;

extracting a dominant frequency from the particular PPG waveform; and determining, by the computing system, the heart rate of the subject based on the dominant frequency extracted from the PPG waveform.

13. The computer system of claim 12, further comprising:

selecting, by the computing system, the regions of interest from the plurality of image frames; and wherein measuring the PPG waveforms extracted from the plurality of image frames comprises, for each region of interest:

averaging, by the computing system, pixels in the region of interest on a per-channel basis to form a plurality of per-channel waveforms; and computing, by the computing system, the PPG waveform as a weighted average of the plurality of per-channel waveforms.

14. The computing system of claim 12, wherein measuring each PPG waveform comprises:

applying one or more bandpass filters to the PPG waveform.

15. The computing system of claim 12, wherein measuring each PPG waveform comprises:

smoothing the PPG waveform using a maximum allowed change in amplitude which is a function of a moving average of PPG waveform values.

16. The computing system of claim 12, wherein extracting the dominant frequency from the particular PPG waveform comprises:

generating a Fast Fourier Transform representation of the PPG waveform; and extracting the dominant frequency from the Fast Fourier Transform representation.

17. The computing system of claim 16, wherein extracting dominant frequency from the Fast Fourier Transform representation comprises:

summing powers of first, second, and third harmonics.

18. The computing system of claim 12, wherein extracting the dominant frequency from the particular PPG waveform comprises:

determining, a signal to noise ratio for each region of interest by computing a ratio between a power of a dominant frequency and powers of non-dominant frequencies on a logarithmic scale;

identifying the region of interest with the largest signal to noise ratio; and extracting the dominant frequency of the region of interest with the largest signal to noise ratio.

19. The computing system of claim 12, wherein the digit comprises a finger.

20. The computing system of claim 12, wherein the digit of the subject is in physical contact with an outermost lens or cover of the camera during capture of the plurality of image frames.

* * * * *